(12) United States Patent
Sporer et al.

(10) Patent No.: US 9,366,285 B2
(45) Date of Patent: Jun. 14, 2016

(54) RETAINING DEVICE FOR AN INSTRUMENT

(75) Inventors: Norbert Sporer, Koenigsdorf (DE);
Matthias Haehnle, Munich (DE)

(73) Assignee: SENSODRIVE GMBH (DE)

( * ) Notice: Subject to any disclaimer, the term of this patent is extended or adjusted under 35 U.S.C. 154(b) by 437 days.

(21) Appl. No.: 13/810,230

(22) PCT Filed: Jul. 14, 2011

(86) PCT No.: PCT/EP2011/003519
§ 371 (c)(1),
(2), (4) Date: Apr. 23, 2013

(87) PCT Pub. No.: WO2012/007168
PCT Pub. Date: Jan. 19, 2012

(65) Prior Publication Data
US 2013/0205558 A1      Aug. 15, 2013

(30) Foreign Application Priority Data

Jul. 15, 2010   (DE) .......................... 10 2010 027 248

(51) Int. Cl.
*B23Q 17/00*    (2006.01)
*F16C 11/10*    (2006.01)
(Continued)

(52) U.S. Cl.
CPC ................. *F16C 11/10* (2013.01); *A61B 19/26* (2013.01); *F16M 11/10* (2013.01); *F16M 11/18* (2013.01);
(Continued)

(58) Field of Classification Search
CPC ............. A61B 19/26; A61B 2019/266; A61B 2019/264; A61B 2019/263; F16M 11/04; F16M 11/10; F16M 11/12; F16M 11/18; F16M 11/2064; F16M 11/2092; F16M 11/2007; F16M 2200/021; F16M 2200/024; F16M 13/027; F16P 3/00; Y10T 29/49764; Y10T 29/49778; Y10T 29/4978; Y10T 403/32262; Y10T 403/32254
See application file for complete search history.

(56) References Cited

U.S. PATENT DOCUMENTS

4,168,881 A * 9/1979 Rosenberger .................. 359/381
5,480,114 A * 1/1996 Nakamura .................. 248/123.2
(Continued)

FOREIGN PATENT DOCUMENTS

| DE | 19526915 A1 | 5/2004 |
|---|---|---|
| DE | 10 2004 008381 A1 | 1/2005 |

(Continued)

OTHER PUBLICATIONS
English machine translation of JP 2001025472.*
(Continued)

*Primary Examiner* — Essama Omgba
(74) *Attorney, Agent, or Firm* — Carter, DeLuca, Farrell & Schmidt, LLP (57) ABSTRACT

A retaining device is provided for an instrument, including at least one joint having at least two parts, and at least one drive unit associated with the joint designed to move the joint by driving at least one of the parts. The retaining device includes a securing device, which has a locking mechanism associated with the joint and a release unit that can be activated, wherein the locking mechanism interacts with the release unit such that the locking mechanism holds the joint in a locked position as long as the release unit is not activated. The securing device permits motion of the joint out of the particular locked position within a specified range of motion even if the release unit is not activated. A corresponding securing device for a retaining device and to an operating method for the securing device are also provided.

13 Claims, 6 Drawing Sheets

(51) Int. Cl.
*F16M 11/10* (2006.01)
*F16M 11/18* (2006.01)
*F16M 11/20* (2006.01)
*F16P 3/00* (2006.01)
*A61B 19/00* (2006.01)
*A61B 17/00* (2006.01)

(52) U.S. Cl.
CPC ............ *F16M 11/2007* (2013.01); *F16P 3/00* (2013.01); *A61B 19/2203* (2013.01); *A61B 19/5223* (2013.01); *A61B 2017/00398* (2013.01); *A61B 2019/263* (2013.01); *A61B 2019/264* (2013.01); *A61B 2019/266* (2013.01); *F16M 2200/021* (2013.01); *F16M 2200/024* (2013.01); *Y10T 29/49764* (2015.01); *Y10T 403/32262* (2015.01)

(56) References Cited

U.S. PATENT DOCUMENTS

| | | | | |
|---|---|---|---|---|
| 5,487,524 A | * | 1/1996 | Bergetz | 248/613 |
| 5,528,417 A | * | 6/1996 | Nakamura | 359/384 |
| 6,364,268 B1 | * | 4/2002 | Metelski | 248/317 |
| 6,957,794 B2 | * | 10/2005 | Landreville et al. | 248/124.2 |
| 7,109,678 B2 | * | 9/2006 | Kraus et al. | 318/560 |
| 7,461,824 B2 | * | 12/2008 | Poxleitner et al. | 248/278.1 |
| 2003/0010877 A1 | * | 1/2003 | Landreville et al. | 248/149 |
| 2004/0190131 A1 | * | 9/2004 | Brenner et al. | 359/384 |
| 2005/0167550 A1 | * | 8/2005 | Poxleitner et al. | 248/125.2 |
| 2007/0156122 A1 | | 7/2007 | Cooper | |
| 2011/0147563 A1 | * | 6/2011 | Metelski | 248/610 |
| 2011/0200320 A1 | * | 8/2011 | Chapman et al. | 396/428 |
| 2014/0366674 A1 | * | 12/2014 | Swartz et al. | 74/490.05 |

FOREIGN PATENT DOCUMENTS

| | | |
|---|---|---|
| DE | 102004004602 A1 | 8/2005 |
| DE | 102004063606 A1 | 7/2006 |
| DE | 102007034286 A1 | 1/2009 |
| EP | 1447700 A2 | 8/2004 |
| EP | 1 520 548 A2 | 4/2005 |
| JP | H10272143 A | 10/1998 |
| JP | 2001-025472 A | 1/2001 |
| JP | 2004-267774 A | 9/2004 |
| JP | 2005-021693 A | 1/2005 |

OTHER PUBLICATIONS

International Search Report for PCT/EP2011/003519 mailed Oct. 28, 2011.

* cited by examiner

RETAINING DEVICE FOR AN INSTRUMENT

The present invention relates to a retaining device for an instrument, said device exhibiting at least one joint, with at least two parts that are movable relative to one another, and at least one drive unit assigned to the joint. The drive unit is designed to move the joint by driving at least one of the parts of the joint that are movable relative to one another.

Driven retaining devices of such a type are already known from the state of the art. Depending upon the type of application, such a retaining device may be a so-called stand device, which retains a medical optical instrument, or a robot with a manipulation unit by way of instrument. As a rule, the joint takes the form of a swivel joint, in which case a load torque is generated in the swivel joint by means of the parts of the joint that are movable relative to one another and by means of the instrument. The drive unit may introduce into the swivel joint a corresponding counter-torque which is suitable to compensate the load torque.

A retaining device of such a type is known, for example, from document DE 10 2004 063 606 A1, wherein the retaining device includes an electric motor for balancing the load torque, which has been combined with means for registering the position of the swivel joint and can be supplied with current in a manner depending on a registered rotary joint position for the purpose of generating a counter-moment balancing the load torque. For this purpose a control unit is provided which sets the requisite motor current.

So-called stand devices or retaining devices for retaining a medical optical instrument are ordinarily employed in order to enable a handling of the instrument that is as easy as possible for the operating surgeon or for further medical staff. Accordingly, by means of the retaining device the medical optical instrument fitted thereto can be brought by hand into a desired position without the weight of the instrument having to be held during the positioning procedure, and the retaining device holds the instrument in the desired position after completion of the positioning procedure.

Ordinarily, the retaining device exhibits a securing mechanism which ensures that the instrument and the retaining device can be moved relatively easily during the positioning procedure and which blocks a movement of the retaining device after completion of the positioning procedure. For this purpose, as specified in document DE 10 2004 063 606 A1, a magnetic brake may be provided in the swivel joint, which, depending on the activation, releases or prohibits a movement of the parts of the swivel joint that are movable relative to one another. If an operator would like to move the retaining device together with the instrument, he/she firstly disengages the magnetic brake, by, for example, pressing a release button, and then moves the instrument by hand into the desired position. As soon as he/she lets go of the release button, the magnetic brake automatically engages again and blocks a further movement of the parts of the swivel joint that are movable relative to one another, so that the retaining device now retains the instrument in the position that has been attained at this time.

While the operator carries out the positioning procedure and keeps the button for releasing the magnetic brake pressed, the electric motor, or generally a drive unit, acts on the movable parts of the swivel joint in such a manner that a load torque introduced into the swivel joint is balanced by a counter-torque, so that the instrument can be displaced in a manner that is virtually weightless for the operator.

By virtue of such a securing mechanism it is made possible that a human operator, such as an operating surgeon for example, and a driven retaining device can be deployed jointly without the retaining device constituting a safety risk for the people located in the working space of the retaining device. The automatic engaging of the brakes as soon as the operator is no longer actuating the securing mechanism prevents the retaining device from moving undesirably into a position in which it may injure a person. The braking action of the brakes is chosen in this case in such a way that the driving force of the drive unit is not sufficient to move relative to one another the parts of a joint at which the brake has been engaged.

One problem that has become known in connection with retaining devices, and also generally in connection with robotic units of all types, consists in the vibration damping of the arrangement. In principle, both unwanted post-oscillations after completion of the procedure for positioning the retaining device and also external building vibrations which, depending on the type of mounting of the retaining device, can be transmitted to the retaining device via the ceiling of the room, side walls of the room or the floor of the room can be introduced into said device and into the instrument connected thereto. Moreover, unwanted vibrations are also introduced into the retaining device and into the instrument by an operator who knocks the retaining device, for example if he/she would like to use the instrument fitted to the retaining device (e.g. would like to look through a microscope). In order to eliminate such unwanted and disturbing vibrations of the instrument on the retaining device as far as possible, from the state of the art it is known to take additional vibration-damping measures.

A first known measure consists in decoupling, in vibration-damping manner, the retaining device from the room in which it is arranged, for example by means of damping intermediate elements which may be arranged between the wall to which the retaining device has been fitted and the retaining device itself. Intermediate elements of such a type can be very elaborate and costly, particularly if they are to be suitable to damp vibrations of highly diverse frequencies. In addition, only building vibrations can be damped in this way, but not the post-oscillations, discussed above, of the retaining device.

As a further measure, from the state of the art it is known to employ systems for active vibration damping in combination with the retaining device. Accordingly, published German patent application DE 10 2004 063 606 A1 discloses a mechanism for active vibration damping, which exhibits a sensor for registering vibrations of the retaining device, which provides a controlled variable for a vibration-damping control loop. This vibration-damping control loop outputs, by way of correcting variable, a superposed motor current to the electric motor, in order thereby to move the swivel joint in such a way that a registered oscillation or vibration of the retaining device is counteracted. A disadvantage of such a configuration, however, is that oscillations or vibrations can only be compensated with this type of vibration damping so long as the brake for securing the position of the retaining device does not block the swivel joint.

However, it may be desirable or necessary to damp vibrations of the retaining device, and consequently also of the instrument, precisely when the retaining device is located in its retaining position (i.e. when the brakes are blocking the at least one swivel joint of the retaining device).

Therefore it is known, moreover, from the state of the art to enable the vibration damping via additional actuators or drive devices which are different from the drive unit for moving the swivel joint. For instance, from document DE 10 2004 004 602 A1 it is known to provide a stand device for a medical optical instrument with an additional drive, in order to enable a vibration damping, whereby the drive may be connected, for example, to a control circuit or control loop.

Document DE 10 2007 034 286 A1 discloses an active vibration-damping device for a stand, which comprises at least one vibration pick-up for picking up a vibration to be damped and at least one additional actuator for generating a damping counter-vibration, wherein the separate actuator may include, for example, piezoelectric elements.

A similar arrangement is also known from document EP 1 447 700 A2, in which an ARES (actively reacting flexible structure) component is employed by way of self-regulating component which, on the basis of the measurement of vibrations, drives integrated drive elements, for example piezoelectric actuators, in such a way that they counteract the vibration in real time, so that the vibrations do not lead to a change of position of the retaining device.

The provision of additional drive elements or damping elements of such a type, however, signifies in each case the necessity to have to integrate additional elements structurally into the configuration of the retaining device. These elements entail an increased effort and hence increased costs not only within the scope of the design process but also during manufacture and assembly. Moreover, an increased inspection effort and/or repair effort may be associated with this, since these additional elements have to be checked regularly as regards their functionality or, in the case of a defect, have to be exchanged or repaired.

Consequently an object of the present invention consists in enabling a cost-effective and reliable vibration damping of the retaining device without a safeguarding, provided by a securing mechanism, of the people located in the working space of the retaining device having to be dispensed with.

This object is achieved by means of a retaining device for an instrument having the aforementioned features, which further exhibits a securing mechanism with a lock assigned to the joint and with a release unit that is capable of being activated, wherein the lock interacts with the release unit in such a manner that it holds the joint in a locking position so long as the release unit has not been activated, wherein the securing mechanism is set up to permit a movement of the joint within a predetermined range of movement out of the respective locking position if the release unit has not been activated.

The securing mechanism of the retaining device according to the invention consequently offers the desired safety which is generally required in the case of an interaction between human and robot, by the robot or the retaining device being able to move completely freely only when the release unit has been activated, that is to say, for example, by a user or operator keeping a release button pressed. If the release unit is deactivated again, then by reason of the specially designed securing mechanism the movement of the joint that is brought about by the drive unit, that is to say, the driven movement of the joint, is possible only within a predetermined range of movement out of the respective locking position, that is to say, out of the position in which the joint was located when the release unit was deactivated.

In this way, for example, a vibration damping can be effected with the aid of the drive unit assigned to the joint also when the retaining device has been locked, since a minimal movement of the joint within the predetermined range of movement suffices for this. At the same time, however, the predetermined range of movement also ensures that the retaining device in the locked state cannot carry out any uncontrolled movement that could endanger the safety of the people located in the working space of the retaining device.

The term 'instrument' here encompasses both optical and/or medical instruments and suchlike as well as a manipulation unit of a robot. Moreover, the use of a retaining device according to the invention may, of course, also be sensible even when no instrument has been fitted to the retaining device.

The lock further includes any non-positive, force-fitting and/or positive, form-fitting type of connection that is able to connect to one another the parts of the joint that are movable relative to one another or is able to connect the drive unit to a part of the joint that is not driven by the drive unit. Further configurations in which the lock connects, for example, the drive unit in non-positive manner or positively to another immovable part of the retaining device, in order to block the latter, are also conceivable.

The joint may take the form of a swivel joint wherein at least one of the parts that are movable relative to one another can be swiveled about an axis of rotation of the swivel joint. Alternatively, however, the joint may also take the form of a sliding joint that enables a linear motion of at least one of the parts that are movable relative to one another. In principle, a design is also conceivable in the form of a joint that permits both a linear motion and a rotational motion of one of the parts of the joint that are movable relative to one another, for example in the form of a screw joint. In practice, however, use has preferably been made hitherto of swivel joints or sliding joints, where appropriate combined with one another.

The release unit may include a handle, a push-button, or any other type of input unit that permits the intention of a user to move the retaining device to be discerned.

The drive unit of the present invention serves for moving the joint by driving at least one of the parts of the joint that are movable relative to one another. Therefore the drive unit—as known from the state of the art—can be utilized to compensate a load torque acting on the joint taking the form of a swivel joint by introducing a counter-torque. Alternatively—that is to say, in the case of a mechanical full or partial compensation of a load torque of such a type, wherein the compensation is effected by virtue of the structural configuration of the retaining device—or in addition, the drive unit may, however, also be utilized for the purpose of vibration damping.

Accordingly, the retaining device may further exhibit a mechanism for active vibration damping, which is configured to output to the drive unit a balancing signal which has the effect that the drive unit moves the joint in such a manner that vibrations of the retaining device can be balanced out. In this case, both torsional vibrations in a joint taking the form of a swivel joint and vibrations in a joint taking the form of a sliding joint can be balanced out.

The drive unit can be controlled in known manner by a control unit which outputs a control signal to the drive unit for the purpose of balancing a load torque which is evoked by the instrument itself and/or by the movable parts of the swivel joint in the joint taking the form of a swivel joint. Said signal has the effect that the drive unit generates in the swivel joint a counter-moment balancing out the load torque (active compensation).

Likewise, in the case of a design of the joint in the form of a sliding joint, the drive unit, controlled by the control unit, can generate a counter-force for balancing a tensile force or compressive force in the joint which is evoked by the force of the dead weight of the joint parts that are movable relative to one another, and of elements, connected thereto, of the retaining device.

If the drive unit is already being actively utilized for the purpose of generating such a counter-moment or such a counter-force, for the purpose of active vibration damping the mechanism outputs to the drive unit a balancing signal which is superimposed on the control signal and in this way brings about the vibration damping.

The same vibration-damping effect can, however, be achieved in the case of a retaining device that does not display active compensation with the aid of the drive unit but rather displays a mechanical full or partial compensation. In the case of a mechanical compensation of a load torque, the retaining device is constructed, for example, in such a manner that the retaining device is held in a state of equilibrium in every possible position by means of balancing weights. The compensation is effected in this case by means of the balancing weights and by means of the balancing effect of the force of the dead weight of the movable parts of the joint. In the case of a mechanical full or partial compensation, the drive unit may consequently be utilized exclusively or at least partly for the purpose of generating the counter-vibration balancing out a vibration.

Both the control unit and the mechanism for active vibration damping may be provided with an internal or external sensor system—for example, sensors for registering the current joint position, for registering the applied load torque or an applied tensile force or compressive force, or for registering vibrations of the retaining device—providing measurement signals which form the basis for the respective control signal or balancing signal.

Moreover, the control unit can be controlled via an external input interface by an operator who, for example, specifies a certain position of the joint. In this way, the drive unit not only serves for vibration damping and, where appropriate, active compensation but can also change the position of the joint, enabling a remote-controlled operation of the retaining device.

The mechanism for active vibration damping may additionally also exhibit an input interface, via which certain inputs can be made by an operator. For instance, the vibration damping can be activated and deactivated or can be limited to a certain vibration range.

The lock may further include at least one stop surface and at least one counter-stop surface, which interact in order to hold the joint in its locking position. In order to enable a lock in two mutually opposed directions of motion of the joint, however, several mutually facing stop surfaces and counter-stop surfaces may be provided.

The stop surface and the at least one counter-stop surface may be arranged on the most diverse parts of the retaining device, for example in each instance on the parts of the joint that are movable relative to one another, on the movable joint part and on an immovable part of the retaining device, on the drive unit and on an immovable part of the retaining device, etc. It only has to be ensured that by this means the joint can be held in a locking position if the release unit has not been activated.

In addition, the lock may include a brake, in particular an electromagnetic brake, whereby a movable part of the brake is coupled with the at least one driven part of the joint and whereby the at least one stop surface of the lock is arranged on the movable part of the brake and the at least one counter-stop surface is arranged on the at least one driven part of the joint. Instead of being coupled with the at least one driven part of the joint, the movable part of the brake may, of course, also be coupled with a drive output of the drive unit, which is connected to the driven part of the joint.

Such a brake makes it possible to block the at least one driven joint part, so that with the aid of the brake the joint is held in the respective locking position that it occupied when the brake was activated. The non-positive design variant of a brake in which the movable part of the brake comes into non-positive, force-fitting abutment with a further immovable part of the brake, which is coupled with the retaining device or with an immovable part of the joint, has the advantage, moreover, that, given an appropriate design of the effective braking force, the joint can still be moved, where appropriate, by hand (by overcoming the maximal braking force or a maximal braking moment resulting therefrom), in order to be able to move the retaining device into a desired position in the case of engaged brakes and in the case of a failure of the retaining device.

Moreover, in particular the configuration of a brake in the form of a closed-circuit brake, for example in the form of an electromagnetic closed-circuit brake, is an advantage, since by reason of its structural configuration said brake exerts a braking force so long as no electrical voltage is applied to it. In this way, it can be ensured that in the case of a possible failure of the power supply of the retaining device the lock can hold said device automatically in a safety position in which an endangerment by virtue of a further, undesired movement of the retaining device is ruled out.

Alternatively or additionally, the lock may exhibit a stop, in particular a stop pin, on which the at least one stop surface is formed and which can engage with a recess having at least two counter-stop surfaces for locking the movement of the joint in two directions of motion. This configuration corresponds to a positive coupling of the movable parts of the joint or of the drive unit with a non-driven part of the joint. In one configuration in the form of a stop pin, the part of the lateral surface of the pin that comes into blocking contact with one of the counter-stop surfaces upon a movement of the joint forms the stop surface.

Such a stop may furthermore be capable of moving back and forth between a first position, in which it locks the movement of the joint, and a second position, in which it permits the movement of the joint. Accordingly, the counter-stop surfaces may be provided as firmly formed surfaces which interact with a retractable and extensible stop or stop pin. The stop pin or stop may furthermore be biased in one of the two positions, for example in the release position, so that upon an activation of the release unit the stop is held in the release position, and upon a deactivation the stop is disengaged and by reason of the bias is automatically moved into the locking position. Possible configurations for such a mechanism include, for example, a spring for biasing the stop in one of the two positions, and a magnet or suchlike for moving and holding the stop into and in the respective other position.

Furthermore, there may be provision that a clearance is provided between the stop surface of the lock and the counter-stop surface in the direction of motion of the joint. The clearance that is provided serves in this case to define the predetermined range of movement within which the joint can move if the release unit has not been activated, that is to say, the retaining device has been locked.

Moreover, there may be provision that at least one elastic intermediate element is provided between the stop surface of the lock and the counter-stop surface in the direction of motion of the joint. This configuration variant can be provided as an alternative to the aforementioned clearance or as an additional measure. In an alternative configuration, the elastic intermediate element replaces the clearance and, by reason of its elasticity, enables a certain movement of the joint within a predetermined range of movement, even when the release unit has not been activated. The range of movement of the joint results in this case by virtue of the elasticity, that is to say, the resilience of the elastic intermediate element, and by virtue of the force or the torque, respectively, acting on the intermediate element and introduced by the drive unit.

By way of such an elastic intermediate element, a rubber element, a rubber coating or suchlike may, for example, be provided. Alternatively, however, configurations of the element formed from an elastic material other than rubber are also conceivable, for example leaf springs or suchlike made of metal. The elastic intermediate element may furthermore be fitted to the stop surface, to the counter-stop surface, or to both surfaces.

By provision of an elastic intermediate element, in addition an automatic centering or alignment of the stop surface in relation to the counter-stop surface as a result of the elastic restoring force of the elastic intermediate element is made possible. In the case of a deactivated release unit, as a result of an acting driving force or an acting torque of the drive unit the stop surface can, moreover, be moved towards the counter-stop surface within the predetermined range of movement. In the process the elastic intermediate element is compressed, and the spacing between the stop surface and the counter-stop surface is diminished. If the driving action of the drive unit, that is to say, the torque acting or the driving force acting, is dispensed with, or if it is reduced so that the elastic restoring force is greater than the remaining driving action, the stop surface is set back relative to the counter-stop surface (alignment) by virtue of the elastic restoring force. In the configuration variant with a stop arranged between two counter-stop surfaces and with two clearance-free elastic intermediate elements between the stop and the counter-stop surfaces, this results in a centering of the stop between the counter-stop surfaces.

As a result of this alignment or centering, it can be ensured that after a free movement of the joint (with release unit activated) the stop surface is always arranged in such a manner with respect to the counter-stop surface that with release unit deactivated the elastic intermediate element can be deformed again, and in this way a further movement of the joint remains possible.

In principle it is also conceivable, however, to configure one or more elements of the retaining device in such a manner that it exhibits or they exhibit an elasticity that suffices to permit a movement of the joint within the predetermined range of movement, and thereby to enable a vibration damping. The range of movement of the joint results in this case by virtue of the resulting elasticity, that is to say, the resulting resilience of the system in the region of the lock, and the force or the torque, respectively, acting on the stop and introduced by the drive unit.

In order, in the configuration variant with a stop, to make it possible that the joint can be locked in any instantaneous position with the aid of the stop, it is advantageous to provide a plurality of recesses with which the stop can engage.

Furthermore, the retaining device may exhibit a monitoring appliance that is suitable to monitor whether the joint is moving within the predetermined range of movement, and to provide a feedback concerning this to the securing mechanism. Such a monitoring appliance may, for example, be connected to the securing mechanism via a communication line, so that the feedback is relayed to the securing mechanism in the form of an input signal to the securing mechanism.

In addition, on the basis of the feedback of the monitoring appliance the securing mechanism can permit an activation of the lock. In this configuration the activation of the lock is effected virtually in two stages: in the first stage, by a deactivation of the release unit the monitoring appliance, which is to monitor whether the joint is being moved within the predetermined range of movement, is activated. So long as this is the case, the lock is not activated, even though the release unit has been deactivated. In the second stage, the monitoring appliance indicates that the movement of the joint has departed from the predetermined range of movement, so the lock is now activated by the securing mechanism and blocks the joint. This ensures that the joint cannot execute any movement going beyond the range of movement that is, for example, useful for vibration damping.

The monitoring appliance may exhibit at least one sensor for monitoring the movement of the joint. Such a sensor may, for example, include a sensor or encoder of the drive unit, for example a visual position sensor or suchlike. It is particularly favorable to use a sensor that is already present in the internal or external sensor system of the control unit or unit for active vibration damping of the retaining device and that is utilized to ascertain a precise position of the swivel joint.

The present invention further relates to a securing mechanism for a retaining device having the features set out above, and also to a working process for it.

The invention will be explained in the following in exemplary manner on the basis of the accompanying schematic Figures. Shown are.

Figure 1:
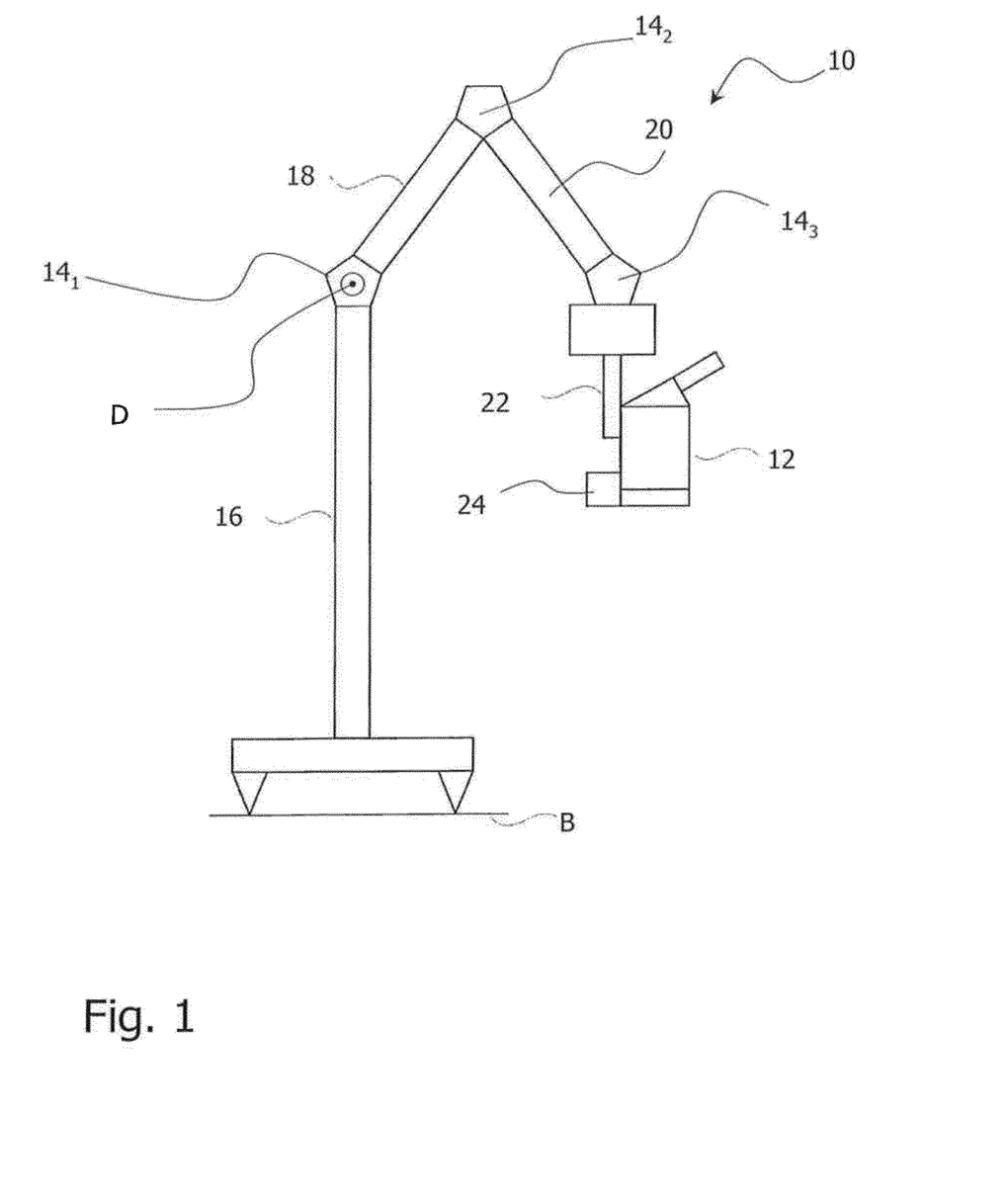
FIG. 1 a schematic side view of a retaining device according to the invention, FIG. 2 a schematic, partially sectioned side view of a swivel joint of a retaining device according to the invention according to FIG. 1, FIGS. 3*a-e* schematic detailed views of the lock mechanism according to FIG. 2, wherein these views show different positions and embodiments of the lock mechanism in perspective representation, FIGS. 4*a* and 4*b* schematic, partially sectioned side views of the lock mechanism according to detail A of FIG. 2, FIG. 5 a schematic, partially sectioned side view of a brake of a retaining device according to the invention according to FIG. 1, FIG. 6 a schematic detailed view of the coupling of the brake according to FIG. 5 with a part of the joint of the retaining device according to the invention, and FIG. 7 a flow chart that describes the procedures within a securing mechanism of the retaining device according to the invention.

In FIG. 1 an embodiment, represented in greatly simplified form, of a retaining device according to the invention is shown in side view. The retaining device is denoted generally by reference symbol 10. The device 10 includes an instrument 12, for example, as illustrated, a microscope or suchlike, which is connected to the retaining device 10. In the embodiment represented in FIG. 1 the retaining device 10 is arranged on the floor B of a room. Alternatively, however, the retaining device 10 could also, of course, have been fitted to the side walls or to a ceiling wall of a room.

The retaining device 10 which is represented is constructed in the form of a so-called stand which exhibits several rigid elements 16, 18, 20 (hereinafter designated as 'arms') which are connected to one another by means of several swivel joints 14. Accordingly, arms 16 and 18 are connected to one another so as to be movable relative to one another by means of swivel joint 14$_1$, and arms 20 and 18 by means of swivel joint 14$_2$. At the free end of the retaining device 10 an instrument receptacle 22 is fitted, which in turn is connected to arm 20 via a swivel joint 14$_3$. Depending on the type and design of the retaining device 10, in this way the instrument 12 can be moved about several axes which may be arranged parallel or transversely to one another. As an alternative to the retaining device 10 shown, the present invention also encompasses, of course, retaining devices that include one or more sliding joints instead of, or in addition to, a swivel joint. Arbitrary joint combinations with variably many and variably designed joints are possible in this connection.

The following remarks on the mode of operation and configuration of swivel joint $14_1$ apply likewise to swivel joints $14_2$ and $14_3$.

Assigned to the individual swivel joints 14 of the retaining device 10 are drive units (not represented), for example in the form of an electric motor or suchlike, which serve to drive at least one of the movable parts of the swivel joint 14 and in this way to move it relative to the other part. Accordingly, as shown in FIG. 2, arm 18 is moved relative to arm 16 by a drive shaft 18a connected to arm 18, exhibiting at its free end an interface 18b via which it can be connected to the drive unit in such a manner that the drive shaft 18a together with arm 18, driven by the drive unit, can move about an axis of rotation D.

Figure 2:
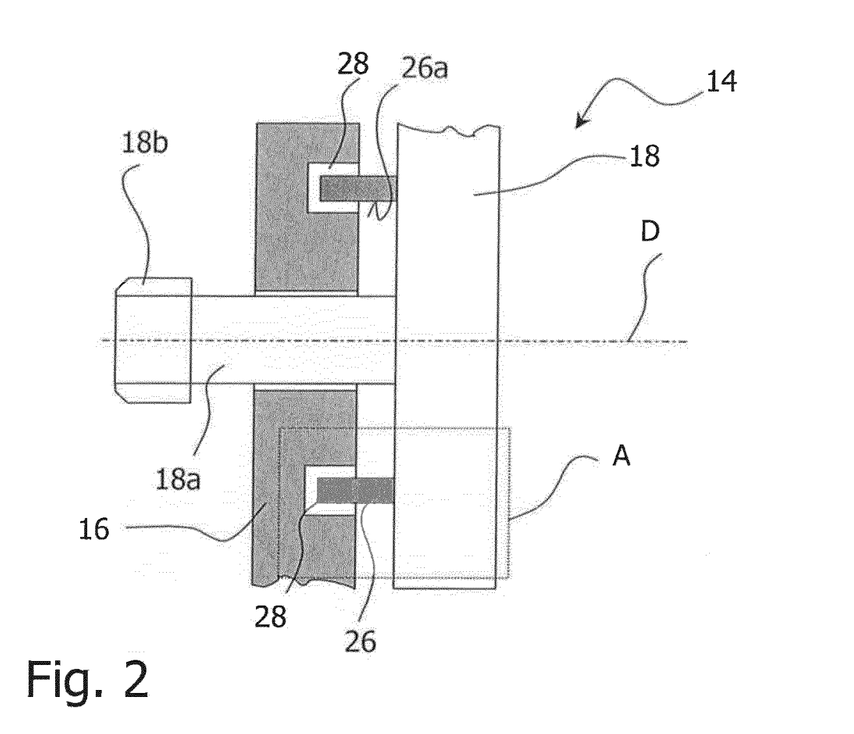

In the embodiment shown in FIG. 2 the drive shaft 18a extends through a through-bore of arm 16, in which connection the shaft 18a may be supported in low-friction manner within the through-bore (not represented). The configuration of the swivel joint 14 represented in FIG. 2 is, however, only exemplary; accordingly, the linkage 18b to a drive unit may also be configured at a different place and in a completely different way, such as, for example, with a drive shaft of the drive unit engaging with arm 18, with a drive unit engaging on the outer contour of arm 18 and suchlike.

Ordinarily in the case of a retaining device, such as the retaining device 10 according to the invention, the drive or the drive unit is provided at each swivel joint 14. Said drive unit may serve to balance out a load torque that is generated in the respective swivel joint 14, caused by the dead weight of the instrument 12 fitted to the retaining device 10 and of the individual elements of the retaining device. For instance, at swivel joint $14_1$ a load torque is generated that results from the weight forces of all the elements connected to arm 18 (inclusive of the instrument 12), and from the associated lever arm.

In order to be able to guarantee a manual handling (manual positioning) of the instrument 12 that is as simple as possible, the drive units in the respective swivel joints 14 serve to balance out the respective load torque by an equally large counter-moment, so that in the case of a manual movement of the instrument 12 in the working space of the retaining device 10 the latter can be moved by an operator in virtually weightless manner, and inertias are also compensated (active compensation). In any case, the friction forces arising in the swivel joints 14, which (with lock disengaged) are slight and depending on the configuration of the retaining device likewise can—as can also inertias arising—be compensated by the drive unit (active compensation), have to be overcome by the operator who would like to move the instrument 12 freely. Alternatively, the retaining device according to the invention may, however, also display in each joint a mechanical full or partial compensation of load torques arising.

As can likewise be discerned in FIG. 2, swivel joint $14_1$ (just like swivel joints $14_2$ and $14_3$) exhibits in addition a lock, for example in the form of a stop pin 26, which serves to couple with one another the parts of swivel joint $14_1$ that are movable relative to one another, in order in this way to block a rotational motion of swivel joint $14_1$. With the aid of the lock the retaining device 10 can retain the desired position after completion of the positioning. As an alternative to a positive coupling, shown in FIG. 2, of the parts 16, 18 of swivel joint $14_1$ which are movable relative to one another, a non-positive coupling is also conceivable, as explained below. In addition, it is equally possible to arrange the lock between the drive unit and the part 16 of swivel joint $14_1$ which is not driven by a drive unit, or between the driven part 18 of swivel joint $14_1$ and an immovable part of the retaining device 10, in order to couple these elements with one another.

A release unit 24 arranged on the instrument 12 forms, together with the lock, a so-called securing mechanism which serves to protect people located in the working space of the retaining device 10 against unintentional movements of the retaining device 10. Accordingly, the retaining device 10 can only be moved freely within its entire working space when the release unit 24 has been activated, whereby in its activated state it interacts with the lock in such a manner that the latter releases the swivel joint 14. As soon as the release unit 24 is not activated, such a free mobility of the retaining device 10 in its working space is no longer to be possible, for safety reasons.

The release unit 24 may include a handle, a push-button, a joystick or any other type of input unit which the user can actuate or activate in order to express the fact that he/she would like to move the retaining device 10.

By reason of its structure, the retaining device 10 according to the invention also offers, besides the manual mobility described above, the possibility to be moved automatically by means of a controller. In principle, a control unit, which is not represented, generates, for example for the purpose of building up a counter-torque in the respective swivel joint 14, a control signal which has the effect that the drive unit drives as desired at least one of the parts of the swivel joint 14 that are movable relative to one another, and in this way moves the swivel joint 14. Once the release unit 24 has been activated, the retaining device 10 may, however, also be moved into a desired position by means of the same control unit or an additional control unit, by the control unit controlling the corresponding drives of the swivel joints 14 (remote-controlled operation).

Moreover, the retaining device 10 is configured in such a manner that vibrations arising, for example due to a post-oscillation of the retaining device 10 after a positioning movement has taken place (manually or automatically) or due to room vibrations which are transmitted to the retaining device 10, for example via the floor B, are damped. This is obtained via a mechanism for active vibration damping (not represented), which uses the drive units of the driven swivel joints 14 for the purpose of vibration damping. To this end, the mechanism for active vibration damping emits to the respective drive unit a balancing signal (where appropriate, superimposed on the control signal) which has the effect that the drive unit moves the swivel joint 14 in such a way that vibrations of the retaining device 10 are compensated. Ordinarily, such a balancing signal is configured in such a manner that it brings about a periodic movement of the swivel joint 14 (exciter vibration) corresponding to the active vibration, whereby by virtue of a phase shift of the exciter vibration relative to the active vibration the active vibration and the exciter vibration cancel each other out.

In order that such an active vibration damping is still possible even when the retaining device is not freely movable in the working space but is to remain in a retaining position, the securing mechanism is set up to permit a movement of the swivel joint 14 out of the respective locking position within a predetermined angular range if the release unit 24 has not been activated.

Figure 3A:
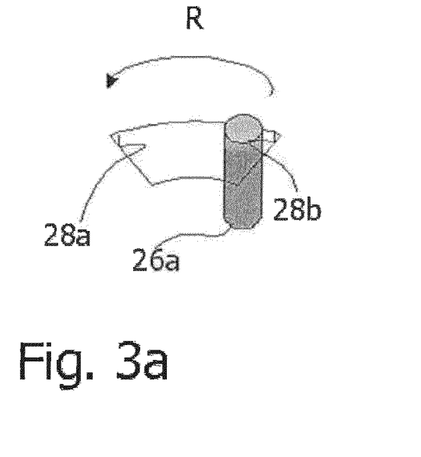
Figure 3B:
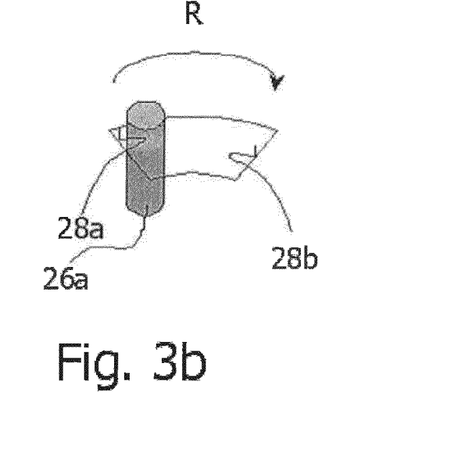
Figure 3C:
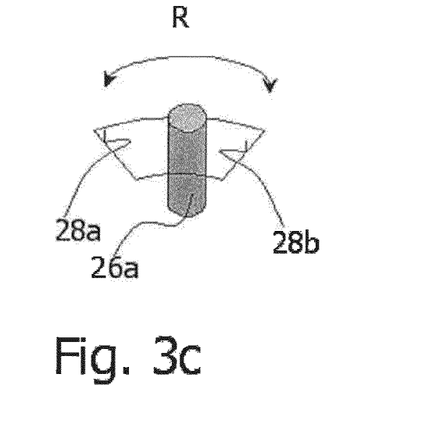
Figure 3D:
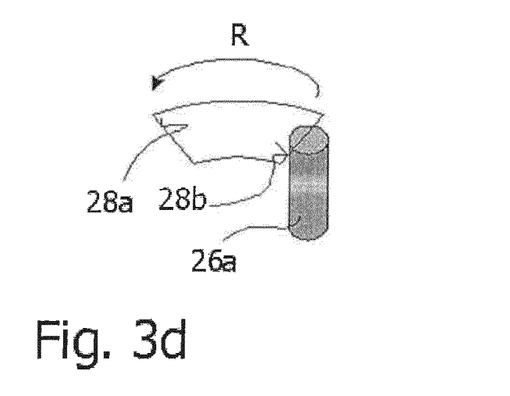
Figure 3E:
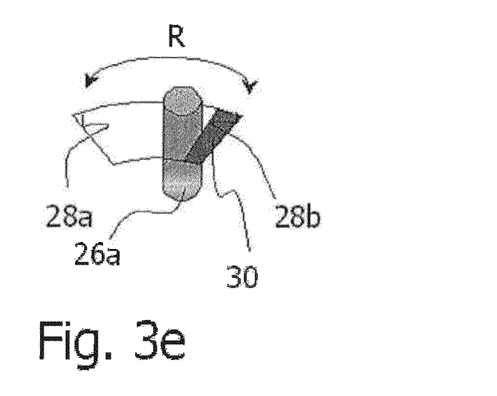
Figure 4A:
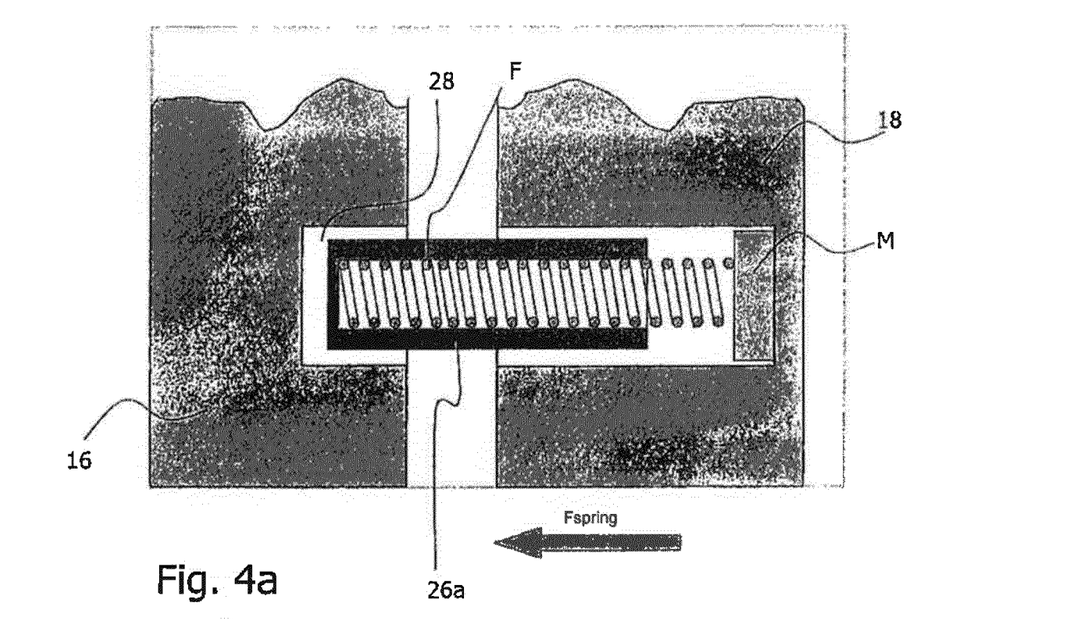
Figure 4B:
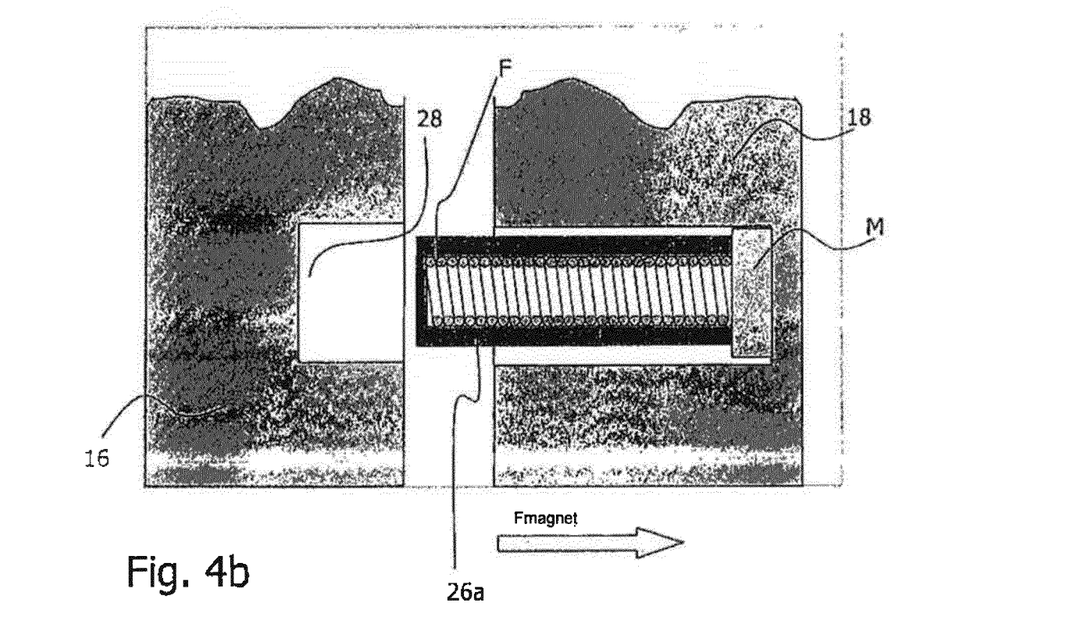

In a first configuration variant, the securing mechanism, as shown in FIGS. 2 to 4b, includes a lock with at least one stop pin 26 (in FIGS. 4a and b, two stop pins 26 are shown), the outer circumferential surface of which forms a stop surface 26a. As represented in FIGS. 4a and 4b, each stop pin 26 can be moved back and forth between a first position, in which it locks the movement of the swivel joint 14, and a second position, in which it permits the movement of the swivel joint. Each stop pin 26 is received in its first position in a recess 28 (in FIGS. 4a and b, two recesses 28 are shown) which exhibits counter-stop surfaces 28a and 28b. Each stop pin 26 may be arranged on the part 18 of swivel joint 14₁ driven by the drive unit or on the non-driven part 16 of swivel joint 14₁, in which case the recesses 28, which provide the counter-stop surfaces 28a and 28b, are arranged on the respective other part of swivel joint 14₁.

The mechanism that is shown for moving the stop pins 26 back and forth comprises, according to FIGS. 4a and 4b, a magnet M and also a spring F. The spring F is received in the interior of the stop pin 26 and biases the latter in such a manner that it is located in the first locking position if the spring F is relaxed. This is also indicated by the arrow $F_{spring}$ in FIG. 4a. Of course, other possible arrangements of the spring F are conceivable.

The magnet M (which is intended to represent schematically a source of magnetic attractive force of any type whatever) serves to relocate the stop pin 26 into the second position thereof (cf. FIG. 4b), in which it permits the movement of the swivel joint 14. For this purpose, a magnetic force, symbolised by the arrow $F_{magnet}$ as shown in FIG. 4b, acts on the stop pin 26, as a result of which the spring F is biased. In the case of the magnet M it is a question not of a permanent magnet but rather of a magnet that is capable of being electrically activated, for example in the form of a coil or suchlike. If the magnet M does not have current applied to it, no magnetic force $F_{magnet}$ acts on the stop pin 26, so that the latter is moved back again into its first position as a result of the spring force $F_{spring}$ of the biased spring F (cf. FIG. 4a).

The mechanism that is shown for moving the stop is purely exemplary and may, for example, be replaced by reversal of action or by using other elements for the introduction of force.

In FIGS. 3a to 3c a possible configuration of the receptacles 28 with the counter-stop surfaces 28a and 28b is shown, in which a stop pin 26 is received in different positions relative to the counter-stop surfaces 28a, 28b. Accordingly, the recess 28 is configured, as clearly perceptible, in such a manner that a clearance is provided between the stop surface 26a of the stop pin 26 and the counter-stop surface 28a or 28b in the direction of motion of the swivel joint 14 (indicated by the arrow R), so that a slight movement of swivel joint 14₁ within a predetermined angular range is possible even when the lock has been activated.

In order to be able to enable a lock of the swivel joint 14 in, as far as possible, any conceivable position, it is necessary to provide a plurality of recesses 28 with corresponding counter-stop surfaces 28a, 28b and also at least two stop pins 26, which are arranged relative to one another and with respect to the counter-stop surfaces 28a, 28b with angular offset (relative to the axis of rotation D) in such a manner that at least one of the stop pins 26 is always capable of engaging with a recess 28, even if the other stop pin is blocked by a counter-stop surface 28b (cf. FIG. 3d).

Moreover, the configuration of the stop pin 26 in the form of a circular cylinder according to FIGS. 2 to 4b and the configuration of the recess according to FIGS. 3a to e are purely exemplary. Accordingly, in an alternative embodiment, for example with conical or sawtooth-shaped stops and corresponding recess surfaces, an unwanted blocking of the movement of the stop pin 26 out of the second position into its first position can be very largely avoided by means of a counter-stop surface 28b (as shown in FIG. 3d).

In addition, instead of, or in combination with, the clearance, discussed above, in the direction R of motion of swivel joint 14₁ it is possible to provide an elastic intermediate element E between the stop surface of the stop and the counter-stop surface 28a, 28b (as shown in FIG. 3e), which permits a further movement of swivel joint 14₁ even when the stop is already bearing against the elastic intermediate element E (cf. FIG. 3e).

The elastic intermediate element E may be arranged either on the counter-stop surface 28a, 28b or on the stop surface 26a. For example, it is conceivable to provide the stop pin 26 or a stop of whatever type with an encasement consisting of an elastic material, for example rubber.

An alternative, non-positive type of lock may include a brake 30 (cf. FIGS. 5 and 6) which couples with one another either the parts 16, 18 of the swivel joint 14 which are movable relative to one another or the drive unit with an immovable part, for example the arm that is not driven by the drive unit (in FIG. 2, arm 16). An example of such a brake 30 is a so-called electromagnetic closed-circuit brake which exhibits a brake disc 32 held under preload, which presses against a corresponding brake stop surface 34 and in this way establishes the force-fit. For this purpose a spring F with a thrust washer 36 presses the brake disc 32 against the corresponding brake stop surface 34. Only when an electrical voltage is applied to the closed-circuit brake is the thrust washer 36 moved by magnetic forces (which are generated by a coil-carrier 38 supplied with current) away from the brake stop surface 34 and contrary to a biasing force $F_{spring}$ of the spring F, so that an axial spacing arises between the brake stop surface 34 and the brake disc 32 of the closed-circuit brake. In this position the force-fit is annulled and the previously braked parts can be moved freely relative to one another.

Figure 5:
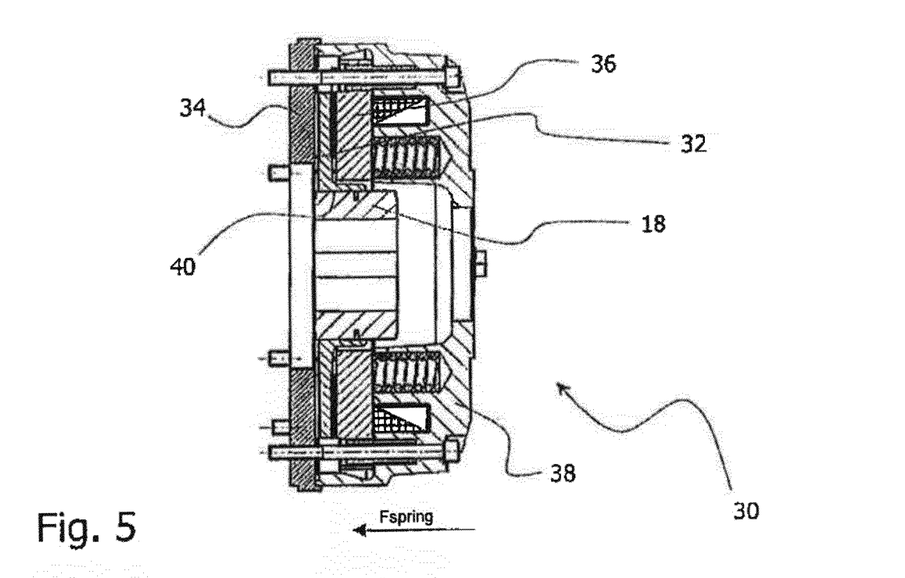
Figure 6:
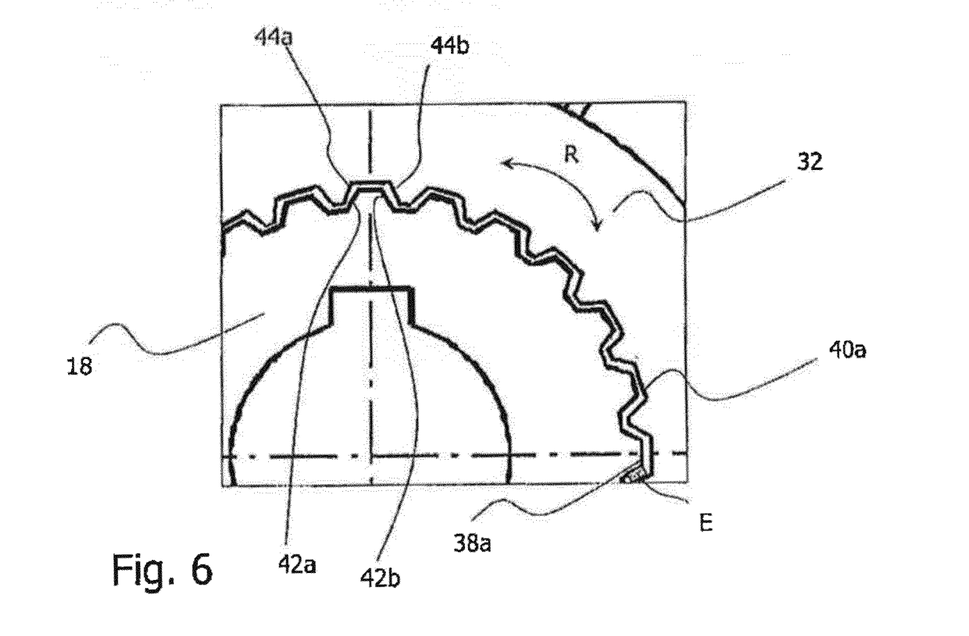

The advantage of such a closed-circuit brake consists, in particular, in the fact that in the event of a possible power failure the brake is automatically activated and in this way the retaining device can be prevented from moving in undesirable manner as a result of its dead weight. A further advantage of a non-positive configuration of the lock—such as, for example, in the form of a brake—consists in the fact that the parts that are movable relative to one another can still be moved, if necessary by overcoming the friction forces of the closed-circuit brake that has been engaged, even when the lock is active, making it possible, in the event of a system failure, to move the retaining device manually out of a position of potential danger.

In the case of the brake 30 shown in FIGS. 5 and 6 the brake disc 32 is coupled with the driven part 18 of swivel joint 14₁, whereas the brake stop surface 34 may, for example, be rigidly connected to the further part 16 of swivel joint 14₁ or to an immovable part of the retaining device 10. The coupling of the brake disc 32 with the driven part 18 is effected via a splined-shaft-like gearing 38a on the outer peripheral surface of a drive shaft 18a of the driven part 18 with a substantially corresponding gearing 40a on the inner peripheral surface of a central recess 40 of the brake disc 32. Each tooth of gearing 38a exhibits two lateral flanks 42a, 42b which form the stop surfaces of the lock according to the invention, whereby the substantially corresponding recesses on gearing 40a each exhibit two flanks 44a, 44b which form the counter-stop surfaces of the lock according to the invention. Between each stop surface and each corresponding counter-stop surface a clearance and/or an elastic element E (in FIG. 6 only one is represented in exemplary manner) is provided in the direction of motion R of part 18, as also explained above in connection with the stop pin 26 with reference to FIGS. 3a to 3c and 3e. The elastic element E serves in this case for the self-centering of the brake disc 32 relative to the drive shaft 18a of the driven part 18, which is linked via the interlocking gearings 38a and 40a.

Figure 7:
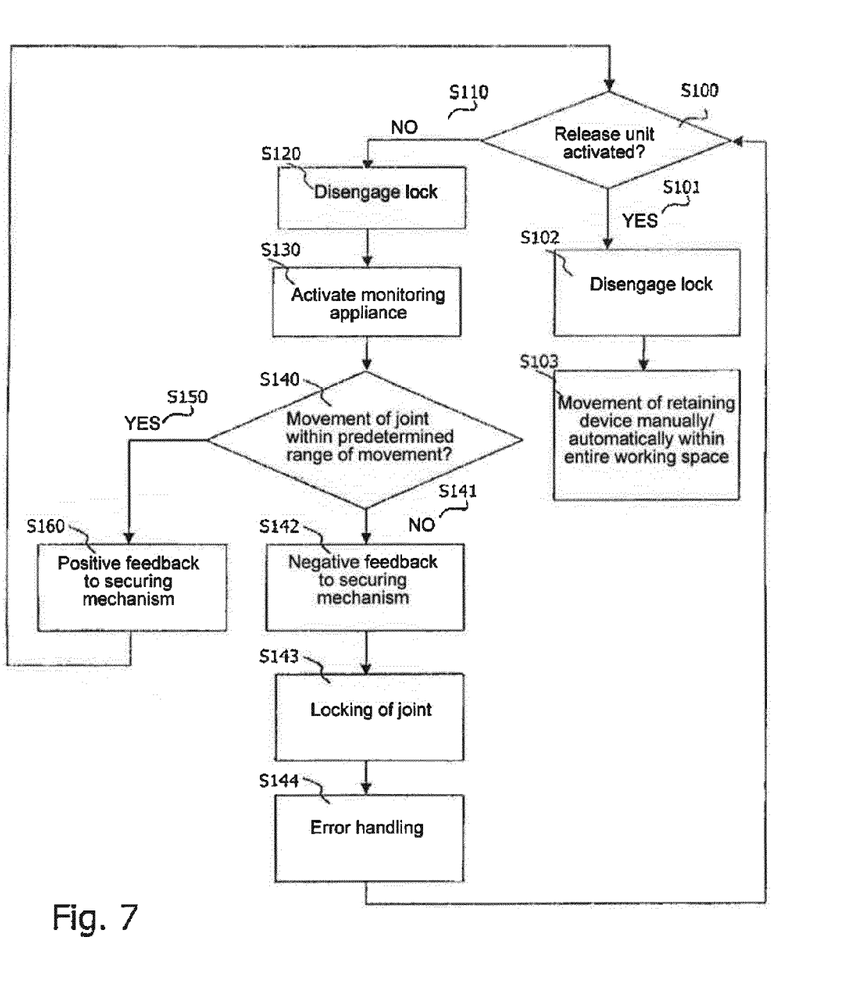

Finally, in FIG. 7 a flow chart is shown which represents in exemplary manner the mode of operation of the securing mechanism of a retaining device 10 according to the invention. In this embodiment, in addition to or as an alternative to the configuration of the lock shown in FIGS. 2 to 6, a software-based control of the securing mechanism is provided.

In a step S100 a controller of the securing mechanism checks whether the release unit 24 has been activated. For this purpose, use may be made, for example, of a conventional push-button switch or sensor of any type, which is arranged on a holding grip, integrated into a push-button or arranged on a different type of input unit and which permits the intention of a user to move the retaining device 10 to be discerned. Upon activation and/or deactivation of the release unit 24, for example by pressure on the corresponding push-button, this push-button switch or sensor emits a signal to the controller of the securing mechanism. If the controller of the securing mechanism receives, in a step S101, the signal that the release unit 24 has been activated, it outputs to the lock a disengage signal, by virtue of which the lock is disengaged (step S102). A prerequisite for this is, of course, that the lock is capable of being controlled, in whatever manner, by the controller. Such a control is possible, for example, in the embodiment shown in FIGS. 4a and 4b, wherein for the purpose of disengaging the lock the magnet M has current applied to it, moving the stop pin 26 into its second position (disengaging position).

After this, in step S103 the retaining device is freely movable manually or automatically within the entire working space of the retaining device 10. If the release unit 24 is deactivated after completion of the desired movement of the retaining device 10, that is to say, if the securing mechanism receives, in a step S110, the signal that the release unit 24 has not been activated, then, in a step S120 it likewise transmits the signal for disengaging the lock (as described above under step S102), but additionally activates, in a step S130, a monitoring appliance (not represented) which monitors the movement of the at least one swivel joint 14 of the retaining device 10. The following remarks are made with reference to a swivel joint 14 but also apply, of course, given a corresponding configuration of the retaining device, to several swivel joints, such as the swivel joints 14₁, 14₂, and 14₃ of the retaining device 10, or to one or more sliding joints.

The monitoring appliance according to the present invention may use, for example, an internal or external sensor system, that is to say, for example, angle sensors by way of internal sensors of the swivel joint 14 (or displacement-measuring sensors for a sliding joint) or external sensors of a navigation sensor system (not represented) etc., in order to obtain a precise indication of the position in which the swivel joint 14 is located (ACTUAL position) and by what angle (or displacement for the sliding joint) the joint 14 has, where appropriate, moved out of the respective locking position (angle of motion or motion displacement).

For this purpose, the monitoring appliance can, for example, store that position of the joint 14 as locking position in which the joint 14 was located at the time at which the securing mechanism received the signal that the release unit 24 has not been activated (step S110). Starting from this locking position, the monitoring appliance can then check whether the joint 14 is being moved out of this locking position within a predetermined range of movement. For this purpose, the monitoring appliance can, for example on the basis of the locking position and the predetermined range of movement, calculate a SET position and can compare the latter with the ACTUAL position or can compare the angle of motion (or motion displacement), ascertained on the basis of the ACTUAL position, with an angle (or displacement) characterizing the SET position (step S140).

In this connection, the predetermined angle or displacement or the range of movement can be adjusted or altered by an operator, depending on the application, or may comprise a fixed safety value. If in the course of a comparison of the ACTUAL position of the joint, or of the angle of motion of the swivel joint 14 (or motion displacement of the sliding joint) with respect to a SET position or the predetermined angle (displacement), the monitoring appliance comes to the conclusion that the joint 14 is being moved within the predetermined range of movement (step S150), it transmits a positive feedback to the securing mechanism (step S160).

A check is then again made as to whether the release unit 24 has been activated (step S100), and in the case of a release unit 24 that is still deactivated the lock remains disengaged (step S120) and the monitoring appliance activated (step S130). If, however, the monitoring appliance recognizes in a step S140 that the movement of the joint 14 threatens to depart from the predetermined range of movement (step S141), it transmits a negative feedback to the securing mechanism (step S142). The latter then causes, in a step S143, a blocking of the joint 14 by outputting a corresponding signal to the lock. In addition, an error handling (S144) is initiated, within the scope of which a check is made as to why the joint 14 is moving beyond the predetermined range of movement (S144).

The mode of operation of the securing mechanism described in FIG. 7 can, of course, be combined with the mechanical configuration of the lock according to FIGS. 2 to 6, whereby, where appropriate, the clearance between the stop surface and the counter-stop surface of the lock is chosen in such a manner that a blocking arises only when the predetermined range of movement for a movement of the joint has been exceeded. In this case the structural configuration serves as an additional safeguard in case the control of the securing mechanism should fail.

The retaining device according to the invention enables, by virtue of its configuration, in particular by virtue of the configuration of the securing mechanism, that, on the one hand, the securing mechanism of the retaining device can continue to ensure the protection of a person located within the working space of the retaining device, and that, on the other hand, also in a retaining position of the retaining device an active vibration damping can take place by utilizing the drive units, which are already present, of the joints.

The invention claimed is:

1. A working process for a securing mechanism, comprising:
   providing the securing mechanism for a retaining device, the securing mechanism including:
   at least one joint, with at least two parts which are movable relative to one another;
   at least one drive unit; and
   a lock assigned to the joint and with a release unit adapted to be selectively activated, wherein the lock holds the joint in a locking position so long as the release unit has not been activated,
   wherein the drive unit is assigned to the joint and is configured to move the joint by driving at least one of the parts of the joint which are movable relative to one another, and
   wherein the securing mechanism permits a movement of the joint out of a respective locking position within a predetermined, limited range of movement even when the release unit has not been activated to enable vibration damping, checking whether the release unit has been activated;

disengaging the lock;

limiting the movement of the joint to a predetermined range of movement if the release unit has not been activated; and activating the lock if the movement of the joint departs from the predetermined range of movement.

2. The working process according to claim 1, wherein the retaining device further comprises a mechanism for active vibration damping configured to output to the drive unit a balancing signal wherein the drive unit moves the joint in such a manner that vibrations of the retaining device can be balanced out.

3. The working process according to claim 1, wherein the lock includes at least one stop surface and at least one counter-stop surface, configured to interact in order to hold the joint in the locking position.

4. The working process according to claim 3, wherein the lock includes a brake with a movable part which is coupled with the at least one driven part of the joint, and wherein the at least one stop surface of the lock is arranged on a movable part of the brake and the at least one counter-stop surface is arranged on the at least one driven part of the joint.

5. The working process according to claim 4, wherein the brake is an electromagnetic brake.

6. The working process according to claim 3, wherein the lock includes a stop on which the at least one stop surface is formed and which can engage with a recess having at least two counter-stop surfaces for locking movement of the joint in two opposite directions of motion.

7. The working process according to claim 6, wherein the stop is movable back and forth between a first position, in which it locks the movement of the joint, and a second position, in which it permits the movement of the joint.

8. The working process according to claim 6, wherein the stop is a stop pin.

9. The working process according to claim 3, wherein a clearance is provided between the stop surface and the counter-stop surface of the lock in a direction of motion of the joint.

10. The working process according to claim 3, wherein at least one elastic intermediate element is provided between the stop surface and the counter-stop surface of the lock in a direction of motion of the joint.

11. The working process according to claim 1, further comprising a monitoring appliance configured to monitor whether the joint is being moved within the predetermined range of movement and to transmit feedback concerning the movement to the securing mechanism.

12. The working process according to claim 11, wherein the securing mechanism can permit an activation of the lock on the basis of the feedback of the monitoring appliance.

13. The working process according to claim 11, wherein the monitoring appliance includes at least one sensor for monitoring the movement of the joint.

* * * * *